(12) United States Patent
Walker et al.

(10) Patent No.: US 8,712,535 B2
(45) Date of Patent: Apr. 29, 2014

(54) LINKED AREA PARAMETER ADJUSTMENT FOR SPINAL CORD STIMULATION AND ASSOCIATED SYSTEMS AND METHODS

(71) Applicant: Nevro Corporation, Menlo Park, CA (US)

(72) Inventors: Andre B. Walker, Monte Sereno, CA (US); Jon Parker, San Jose, CA (US)

(73) Assignee: Nevro Corporation, Menlo Park, CA (US)

( * ) Notice: Subject to any disclaimer, the term of this patent is extended or adjusted under 35 U.S.C. 154(b) by 0 days.

(21) Appl. No.: 13/914,494

(22) Filed: Jun. 10, 2013

(65) Prior Publication Data

US 2014/0031893 A1   Jan. 30, 2014

Related U.S. Application Data

(63) Continuation of application No. 12/510,930, filed on Jul. 28, 2009, now Pat. No. 8,498,710.

(51) Int. Cl.
*A61N 1/00* (2006.01)
(52) U.S. Cl.
USPC ................................. 607/46; 607/2; 607/116
(58) Field of Classification Search
USPC ................................. 607/2, 46, 116
See application file for complete search history.

(56) References Cited

U.S. PATENT DOCUMENTS

| | | | |
|---|---|---|---|
| 4,210,151 A | 7/1980 | Keller, Jr. | |
| 4,340,063 A | 7/1982 | Maurer | |
| 5,016,635 A | 5/1991 | Graupe | |
| 5,063,929 A | 11/1991 | Bartelt et al. | |
| 5,159,926 A | 11/1992 | Ljungstroem | |
| 5,184,617 A | 2/1993 | Harris et al. | |
| 5,222,494 A | 6/1993 | Baker, Jr. | |
| 5,540,730 A | 7/1996 | Terry, Jr. et al. | |
| 5,938,690 A | 8/1999 | Law et al. | |
| 6,308,102 B1 | 10/2001 | Sieracki et al. | |
| 6,353,762 B1 | 3/2002 | Baudino et al. | |
| 6,381,496 B1 | 4/2002 | Meadows et al. | |
| 6,440,090 B1 | 8/2002 | Schallhorn | |
| 6,516,227 B1 | 2/2003 | Meadows et al. | |
| 6,587,727 B2 | 7/2003 | Osorio et al. | |
| 6,609,030 B1 | 8/2003 | Rezai et al. | |
| 6,622,048 B1 | 9/2003 | Mann et al. | |

(Continued)

OTHER PUBLICATIONS

International Search Report and Written Opinion, International Application No. PCT/US10/043569, Applicant: Nevro Corporation, mailed Sep. 28, 2010, 15 pages.

(Continued)

*Primary Examiner* — Nicole F Lavert
(74) *Attorney, Agent, or Firm* — Perkins Coie LLP (57) ABSTRACT

Systems and methods for managing pain in a patient using an electrical waveform that link the modulation of a waveform parameter for different areas of a patient. One embodiment in a system for managing pain in a patient comprises an electric device configured to be implanted into the patient and including a plurality of electrodes having at least a first electrode associated with a first area of the patient and a second electrode associated with a second area of the patient. The system further includes an implantable device configured to be coupled to the electrode device and having a computer-operable medium programmed to change the waveform parameter applied to the first electrode and automatically set the waveform parameter applied to the second electrode based on a relationship between a first therapy range and a second therapy range of the waveform parameter.

25 Claims, 9 Drawing Sheets

(56) References Cited

U.S. PATENT DOCUMENTS

| | | |
|---|---|---|
| 6,947,792 B2 | 9/2005 | Ben-Haim et al. |
| 7,020,523 B1 | 3/2006 | Lu et al. |
| 7,050,856 B2 | 5/2006 | Stypulkowski |
| 7,110,821 B1 | 9/2006 | Ross |
| 7,127,296 B2 | 10/2006 | Bradley |
| 7,174,215 B2 | 2/2007 | Bradley |
| 7,239,920 B1 | 7/2007 | Thacker et al. |
| 7,239,926 B2 | 7/2007 | Goetz |
| 7,242,984 B2 | 7/2007 | DiLorenzo |
| 7,263,402 B2 | 8/2007 | Thacker et al. |
| 7,266,412 B2 | 9/2007 | Stypulkowski |
| 7,343,200 B2 | 3/2008 | Litvak et al. |
| 7,463,927 B1 | 12/2008 | Chaouat |
| 7,747,330 B2 | 6/2010 | Nolan et al. |
| 7,945,330 B2 | 5/2011 | Gliner et al. |
| 7,957,814 B2 | 6/2011 | Goetz et al. |
| 8,498,710 B2 | 7/2013 | Walker et al. |
| 2003/0093134 A1 | 5/2003 | Bradley |
| 2003/0153959 A1 | 8/2003 | Thacker et al. |
| 2003/0195582 A1 | 10/2003 | Mann |
| 2004/0167584 A1 | 8/2004 | Carroll et al. |
| 2005/0060001 A1 | 3/2005 | Singhal et al. |
| 2005/0060007 A1 | 3/2005 | Goetz |
| 2005/0245987 A1 | 11/2005 | Woods et al. |
| 2006/0195159 A1 | 8/2006 | Bradley et al. |
| 2006/0259099 A1 | 11/2006 | Goetz et al. |
| 2008/0046036 A1 | 2/2008 | King et al. |
| 2008/0183256 A1 | 7/2008 | Keacher |
| 2008/0234791 A1 | 9/2008 | Arle et al. |
| 2009/0018617 A1 | 1/2009 | Skelton et al. |
| 2009/0112282 A1 | 4/2009 | Kast et al. |
| 2009/0281599 A1 | 11/2009 | Thacker et al. |
| 2010/0125314 A1 | 5/2010 | Bradley et al. |
| 2010/0131034 A1 | 5/2010 | Gliner et al. |
| 2010/0274312 A1 | 10/2010 | Alataris et al. |
| 2012/0083857 A1 | 4/2012 | Bradley et al. |
| 2012/0130448 A1 | 5/2012 | Woods et al. |

OTHER PUBLICATIONS

Keuchmann C et al., "853 Could Automatic Position Adaptive Stimulation be Useful in Spinal Cord Stimulation," Abstract, Medtronic, Inc., undated, 1 page.

LINKED AREA PARAMETER ADJUSTMENT FOR SPINAL CORD STIMULATION AND ASSOCIATED SYSTEMS AND METHODS

CROSS-REFERENCE TO RELATED APPLICATION

This application is a continuation of U.S. patent application Ser. No. 12/510,930, filed on Jul. 28, 2009, entitled LINKED AREA PARAMETER ADJUSTMENT FOR SPINAL CORD STIMULATION AND ASSOCIATED SYSTEMS AND METHODS, which is incorporated herein by reference in its entirety.

TECHNICAL FIELD

The present technology is directed generally to spinal cord stimulation for managing pain, and associated systems and methods related to adjusting the amplitude, duty cycle and/or other parameters of the electrical waveform applied to the patient.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings or bands spaced apart from each other at the distal end of the lead body. The conductive rings operate as individual electrodes and, in many cases, the SCS leads are implanted percutaneously through a large needle inserted into the epidural space either with or without the assistance of a stylet.

Once implanted, the pulse generator applies electrical signals via the electrodes to modify the function of the patient's nervous system, such as altering the patient's responsiveness to sensory stimuli and/or altering the patient's motor-circuit output. In pain treatment, the electrical signals can generate sensations which mask or otherwise alter the patient's sensation of pain. For example, in many cases patients report a tingling or paresthesia that is perceived as more pleasant and/or less uncomfortable than the underlying pain sensation. Although this may be the case for many patients, many other patients may report less beneficial effects and/or results. Accordingly, there remains a need for improving the techniques and systems for addressing patient pain.

One particular challenge of implementing neurological stimulators to manage pain is that multiple parts or regions of the patient's body contribute to the pain perceived by the patient, and the individual contributions of the various regions vary over time. For example, patients generally experience different levels of back pain and/or lower extremity pain because of exertion, stress, movement (e.g., walking, bending, twisting, etc.), position (e.g., standing, sitting, etc.), and other factors. Patients accordingly change the parameters of the electrical waveform in some or all of the affected regions on an ongoing basis to effectively manage the pain.

DETAILED DESCRIPTION

The invention herein described can be implemented in numerous ways, including as a process, a method, a routine, a device, an apparatus, a system, a composition of matter, an electrical waveform, a computer readable or operable medium such as a computer readable storage medium or a computer network wherein program instructions that are sent over optical or electronic communication links. In this specification, these implementations, or any other form that the invention may take, may be referred as present technology or invention.

The present technology is directed generally to spinal cord stimulation (SCS) systems and methods for managing pain in a patient using an electrical waveform (e.g., electrical signals). Specific details of certain embodiments of the disclosure are described below with reference to changing one or more parameters of the electrical waveform applied to different areas of the patient using a spinal cord stimulator. The disclosed systems and methods, however, may be used in the context of other stimulators and/or other patient conditions. Accordingly, some embodiments of the technology can have configurations, components, or procedures different than those described in this section, and other embodiments may eliminate particular components or procedures described below. A person of ordinary skill in the relevant art, therefore, will understand that the technology may have other embodiments with additional elements and/or other embodiments without several of the features shown and described below with reference to FIGS. 1A-7.

Overview

During the trial period and the course of the SCS therapy itself, the patients typically change the parameters of the waveforms applied to different areas along the spinal cord to optimize the therapy. For example, if the patient experiences leg and/or back pain that varies over time, patient position, and other factors, the patient inputs change commands via a patient programmer that causes the pulse generator to increase or decrease one or more parameters of the electrical waveform. In most SCS systems, the amplitude is the parameter that can be modulated by the patient. Current SCS systems and processes, however, use complex devices with multiple settings to change the amplitude across multiple areas. Conventional systems usually include a manual mode in which the patient experimentally determines a suitable combination of areas and the amplitudes to apply to those areas. Because patients typically perform this on a trial-and-error basis, it is often only marginally effective and time consuming. Conventional systems may also include a linked mode in which the amplitudes of the waveform applied to one or more areas are tied together so that the patient merely adjusts the amplitude. Conventional linked mode systems adjust the amplitudes equally across each area, but this can be ineffective because different areas typically have different maximum amplitude thresholds above which the patient experiences increased pain levels. As a result, existing linked mode systems are limited because the amplitude can only be adjusted to the extent that the stimulation does not exceed the level of the area having the lowest maximum amplitude threshold. Certain aspects of the present technology simplify this process and enhance the ability to quickly change the amplitude or other waveform parameter across a plurality of areas.

In some embodiments, the present technology includes an electrode device having a plurality of electrodes including at least a first electrode associated with a first area of the patient and a second electrode associated with a second area of the patient. The first area has a first therapy range for a waveform parameter, and the second area has a second therapy range for the waveform parameter. The electrode device may be configured to be implanted into a patient. The technology further includes a power supply, a waveform generator configured to generate the waveform and a computer readable medium operatively coupled to the waveform generator. In some embodiments, the technology further includes an implantable device configured to be coupled to the electrode device and the implantable device includes the power supply, the waveform generator configured to generate the waveform, and the computer-operable medium operatively coupled to the waveform generator.

The technology can include delivering an electrical waveform at a first level of the waveform parameter to a first electrode located at the first area and at a second level of the waveform parameter to a second electrode at the second area. The technology can further include changing the first level of the waveform parameter to an updated first level, setting the second level of the waveform parameter based on the scaling factor to an updated second level, and delivering the electrical waveform at the updated first level of the waveform parameter to the first electrode and at the updated second level of the waveform parameter to the second electrode. In the various embodiments, this can include changing the first level of the waveform parameter, automatically setting the second level of the waveform parameter based on a ratio or other relationship between the first therapy range and the second therapy range, and delivering the electrical waveform to the first electrode and at the first level to the second electrode at the second level.

In some embodiments the computer-operable medium is programmed to change the waveform parameter applied to the first electrode and automatically set the parameter for the waveform applied to the second electrode based on a relationship between the first therapy range and the second therapy range (e.g., a therapy range ratio or other scaling factor). For example, when a change command is received by the implantable device, the computer-operable medium can be programmed to (a) change the waveform parameter applied to the first electrode by a first increment and (b) set the waveform parameter applied to the second electrode by a second increment in direct proportion to a therapy range ratio of the first therapy range to the second therapy range. In a different example, when a set of change commands is received, such as by the implantable device, the computer-operable medium is programmed to (a) change the waveform parameter applied to the first electrode by a change increment for each change command received by the implantable device and (b) set the waveform parameter applied to the second electrode according to a best-fit approximation of the therapy range ratio. In this latter example the computer-operable medium can be programmed to set the waveform parameter applied to the second electrode either by changing the parameter applied to the second electrode by the same amount as the first electrode or by holding the parameter applied to the second electrode constant when the patient inputs a change command.

In some embodiments, the technology further includes determining and/or receiving a scaling factor of the waveform parameter based on a relationship between the first and the second therapy ranges. The computer-operable medium can be programmed to receive a predetermined scaling factor of a waveform parameter based upon a relationship between a first therapy range for the waveform parameter at a first area of the patient and a second therapy range for the waveform parameter at a second area of the patient. Alternatively, the computer-operable medium can automatically calculate the scaling factor based upon the first and second therapy ranges.

In some embodiments, the technology further includes delivering an electrical waveform at a first level of the waveform parameter to the first electrode located at the first area of the patient and at a second level of the waveform parameter to the second electrode, and delivering an updated first level to the first electrode and delivering an updated second level of the waveform parameter to the second electrode. In one particular example, the computer program is programmed to change the level of the waveform parameter applied to the first electrode implanted at the first area of the patient to an updated first level, automatically set the second level of the waveform parameter based on a ratio or other relationship between the first therapy range and the second therapy range to an updated second level, and deliver the electrical waveform at the updated first level to the first electrode and at the updated second level to the second electrode.

In some embodiments, the computer-operable medium is programmed to prevent the waveform parameter applied to the first area from exceeding a first maximum and/or preventing the waveform parameter applied to the second area from exceeding a second maximum.

The waveform parameters for the foregoing technology can include the amplitude, impedance, voltage, pulse width, frequency, duty cycle and other parameters. For example, the waveform parameter can include the power delivered via the first electrode and/or the second electrode over a given period of time.

Representative Systems and Methods

Figure 1A:
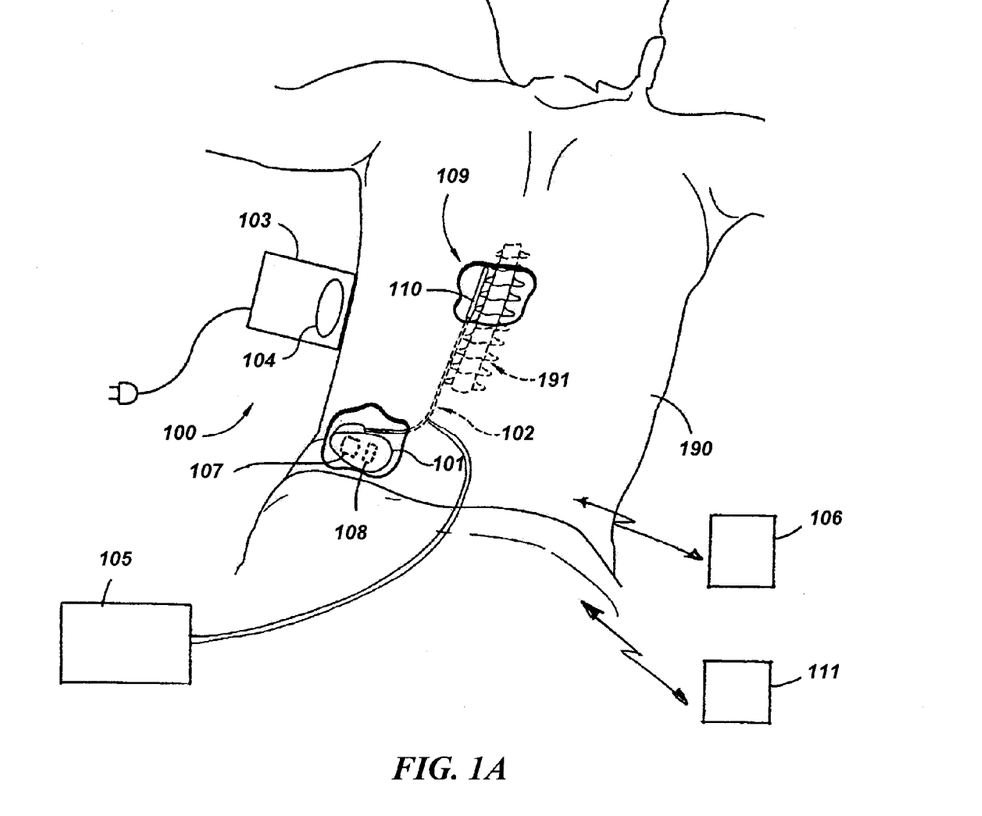
FIG. 1A is a partially schematic illustration of an implantable spinal cord stimulation system positioned at the spine to deliver therapeutic signals in accordance with an embodiment of the present technology.
Figure 1B:
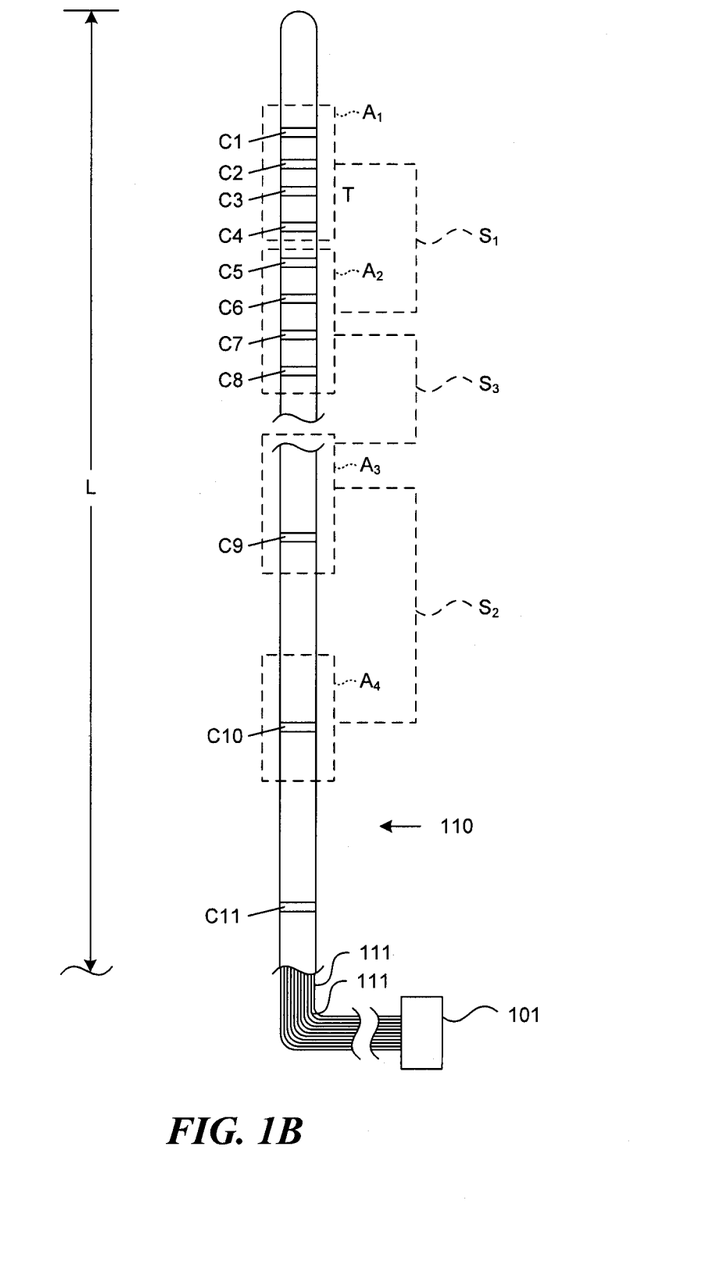
FIG. 1B is a partially schematic illustration of a lead having electrode contacts that form elements of one or more therapy circuits associated with different areas of the patient that are modulated in accordance with methods of the present technology.

In the following discussion, FIGS. 1A-1B illustrate a representative implementation of a system 100 implanted in the spinal cord region of a patient 190, and FIGS. 2-7 illustrate representative components of system, methods, routines, associated circuits, and/or waveforms for managing pain across multiple areas of a patient. FIG. 1A schematically illustrates the treatment system 100 arranged relative to the general anatomy of the patient's spinal cord 191 to provide relief from chronic pain and/or other conditions. The system 100 can include a waveform generator 101, which may be implanted subcutaneously within the patient 190 and coupled to an electrode device 109 (e.g., a signal delivery element). In a representative example, the electrode device 109 includes a lead or lead body 110 that carries features or elements for delivering therapy to the patient 190 after implantation. The waveform generator 101 can be connected directly to the lead body 110, or it can be coupled to the lead body 110 via a communication link 102 (e.g., an extension). As used herein, the terms lead and lead body include any of a number of suitable substrates and/or support members that carry devices for providing therapy signals to the patient 190. For example, the lead body 110 can include one or more electrodes or electrical contacts that direct electrical signals into the patient's tissue. In other embodiments, the electrode device 109 can include devices other than a lead body (e.g., a paddle) that also direct electrical signals and/or other types of signals to the patient 190.

The waveform generator 101 can transmit electrical signals (i.e., waveforms) to the electrode device 109 that up-regulate (e.g., stimulate or excite) and/or down-regulate (e.g., block or suppress) target nerves. As used herein, and unless otherwise noted, the terms "stimulate" and "stimulation" refer generally to signals that have either type of effect on the target nerves, and the terms "electrical signals" and "electrical waveforms" are used interchangeably. The waveform generator 101 can include a machine-readable medium (e.g., computer-operable medium or computer-readable medium) programmed or otherwise containing instructions for generating and transmitting suitable therapy waveforms. The waveform generator 101 and/or other elements of the system 100 can include one or more processors 107, memories 108 and/or input/output devices. Accordingly, the process of managing pain across multiple areas can be performed by computer-executable instructions contained on computer-operable media, e.g., the processor(s) 107 and/or memory(s) 108. The waveform generator 101 can include multiple portions, elements, and/or subsystems (e.g., for directing signals in accordance with multiple signal delivery parameters) contained in a single housing, as shown in FIG. 1A, or contained in multiple housings. In any of these embodiments, the waveform generator 101 and/or other implanted components of the system 100 can include elements for detecting and responding to patient movement, impedance changes or other variables.

In some embodiments, the waveform generator 101 receives power from an external power source 103. The external power source 103 can transmit power to the implanted waveform generator 101 using electromagnetic induction (e.g., RF signals). For example, the external power source 103 can include an external coil 104 that communicates with a corresponding internal coil (not shown) within the implantable waveform generator 101. The external power source 103 can be portable and rechargeable for ease of use.

In another embodiment, the waveform generator 101 can receive power from an internal power source in addition to or in lieu of the external power source 103. For example, the implanted waveform generator 101 can include a battery that is either non-rechargeable or rechargeable to provide the power. When the internal power source includes a rechargeable battery, the external power source 103 can be used to recharge the battery. The external power source 103 can in turn be recharged from a suitable power source (e.g., conventional wall power).

In some cases, an external programmer 105 (e.g., a trial stimulator) can be coupled to the electrode device 109 during a trial procedure before implanting the waveform generator 101. A practitioner (e.g., a physician and/or a company representative) can use the external programmer 105 to vary the stimulation parameters provided to the electrode device 109 in real time, and select optimal or particularly efficacious parameters. During the trial period, the practitioner can also vary the position of the electrode device 109. After the position of the electrode device 109 and initial signal delivery parameters are established using the external programmer 105, the trial period continues for a limited time period by providing the therapy to the patient 190 via signals generated by the external programmer 105. In a representative application, the patient 190 receives the trial therapy for one week. If the trial therapy is effective or shows the promise of being effective, the practitioner then replaces the external programmer 105 with the implanted waveform generator 101. The practitioner can optionally replace or reposition the electrode device 109 at the same time. The waveform parameters are initially based on the experience of the trial period, but these parameters can be further adjusted remotely via a wireless physician's programmer (e.g., a physician's remote) 111 and/or a wireless patient programmer 106 (e.g., a patient remote) at any time. Generally, the patient 190 has control over fewer parameters than the practitioner. For example, the capability of the patient programmer 106 may be limited to starting/stopping the waveform generator 101 and adjusting the stimulation amplitude applied to one or more areas adjacent the electrode device 109.

In any of the foregoing embodiments, the waveform parameters can be modulated during portions of the therapy regimen across one or more of the areas adjacent the electrode device 109. For example, the frequency, amplitude, pulse width, duty cycle, and/or signal delivery location can be modulated in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation. In accordance with the present technology, one or more sets of areas adjacent to the signal delivery element 109 are linked together for the purpose of modulating one or more of the waveform parameters based on a scaling factor between the individual areas in each set. As explained in more detail below, the level of a waveform parameter applied to each area in a linked pair can be modulated based upon a scaling factor between the corresponding areas.

FIG. 1B illustrates a representative lead 110 that can be connected to the waveform generator 101. The lead 110 can have any suitable number of contacts C positioned along its length L for delivering electrical therapy to the patient. For purposes of illustration, the lead 110 can have 11 contacts C (identified individually as contacts C1, C2 . . . C11). In operation, one or more of the contacts C is cathodic and another one or more of the contacts C is anodic. The contacts C can be individually addressable so that any contact C or combination of contacts C can operate as a cathode, and any contact C or combination of contacts C can operate as an anode. The contacts C can be electrically grouped in any of a wide variety of combinations, and individual contacts C can perform different functions (e.g., cathodic functions and/or anodic functions) at different times during the course of a therapy regimen. In any of these embodiments, each contact C may be coupled with a corresponding conductor 111 to the waveform generator 101. The conductors 111 may have one or more connection points along their lengths (e.g., at a junction with the waveform generator 101, and optionally at a junction with an extension). Accordingly, the circuit for a given pair of contacts C includes the contacts C, the patient tissue T between the contacts, the individual conductors 111, connection points along the conductors 111, and connection points between the conductors 111 and the waveform generator 101.

Figure 2:
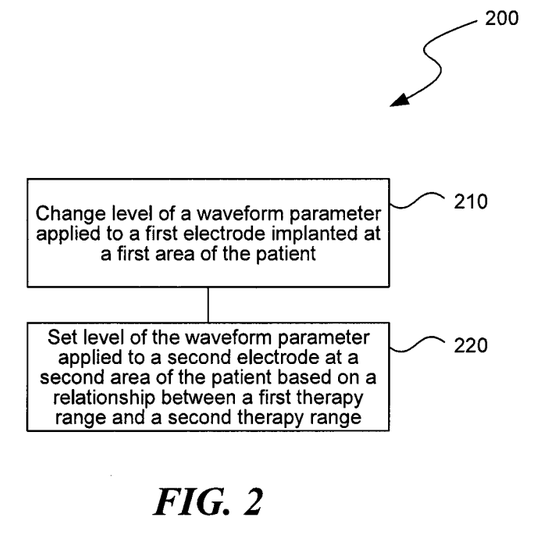
FIG. 2 is a flow diagram illustrating a process for managing pain using linked area parameter modulation.

FIG. 2 illustrates an overall process in accordance with a specific embodiment of the technology for managing pain in a patient using an electrical waveform. In this embodiment, the patient has a first area which has a first therapy range for a waveform parameter and a second area which has a second therapy range for the waveform parameter. The method 200 can include changing the level of the waveform parameter applied to a first electrode located at the first area of the patient (block 210), and automatically setting the level of the waveform parameter applied to a second electrode located at the second area of the patient (block 220). The level of the waveform parameter applied to the second electrode is automatically set by the computer-operable medium based on the magnitude of the change of the waveform parameter applied to the first electrode and a relationship between the first therapy range and the second therapy range (block 220). The waveform parameter, for example, can be the amplitude, pulse width, duty cycle, frequency, power or other variable. The relationship between the first therapy range and the second therapy range can be a scaling factor that compensates for different sensation, therapy and pain thresholds between the first and second areas. The method 200 accordingly links the level of the waveform parameter applied to the second area of the patient to the level of the waveform parameter applied to the first area of the patient based on the relationship between the first and second therapy ranges for the waveform parameter.

The method 200 is not limited to linking the adjustment of the level of a single waveform parameter across different areas of the patient, but rather the method 200 can include linking changes in the levels of a set of parameters of the waveform applied to one area of the patient to the levels of the same set of parameters of the waveform applied to another area of the patient based on the scaling factor. The method 200 is also not limited to linking the adjustment for the level of just the first and second areas of the patient, but rather the method 200 can include linking the level of the waveform parameter to any number of areas of the patient's body in addition to, or in lieu of, linking the waveform parameter applied to the first and second electrodes located at the first and second areas of the patient. The use of "first" and "second" throughout is accordingly inclusive of additional like features, and thus unless otherwise expressly stated the use of "first" and "second" throughout does not exclude any additional like or similar features. In several embodiments, the method 200 includes changing the level of the waveform parameter applied to the first electrode and concurrently setting the level of the waveform parameter applied to the second electrode, but in other embodiments there can be a delay between changing the level of the waveform parameter applied to the first electrode and setting the level of the waveform parameter applied to the second electrode.

The different areas of the patient can be sites relative to the patient's spinal cord. For example, the first and second areas can be located adjacent to the patient's spinal cord such that the electrical waveform applied to the first area affects a first population of neurons while the waveform applied to the second area affects a second population of neurons. The first and second neuron populations can be completely distinct from each other, or in other situations there can be some overlap among the different neuron populations.

The different areas of the patient are generally associated with different areas of pain perceived by the patient. Referring to FIG. 1B, for example, any of the electrodes C1-C11 can be associated with individual areas of the patient to apply energy to different populations of neurons that control or are otherwise involved in the transmission of pain signals associated with different regions of the patient. The method 200 can further include locating more than one electrode at each individual area of the patient. For example, electrodes C1-C4 can be located at a first area $A_1$ of the patient, electrodes C5-C8 can be located adjacent to a second area $A_2$ of the patient, electrode C9 can be located adjacent to a third area $A_3$ of the patient, and electrode C10 can be located at a fourth area $A_4$ of the patient. In other embodiments, only a single one of the electrodes C1-C11 can be located and/or activated at a single area of the patient. The configuration of areas $A_1$-$A_4$ shown in FIG. 1B is merely one example, and a person skilled in the art of implementing SCS systems will understand that the number of areas and the number of electrodes per area varies and are not limited to those shown in FIG. 1B.

The method 200 links the modulation of at least one waveform parameter across two areas of the patient. For example, two or more of the different areas of the patient $A_1$-$A_4$ can be linked together in one or more sets in which a scaling factor is applied to changes of a waveform parameter between the different areas of a set. In one embodiment, areas $A_1$ and $A_2$ can be linked together to define a first area set in which a scaling factor $S_1$ is applied to the waveform parameter applied to each of the areas $A_1$ and $A_2$. Similarly, the third area $A_3$ and the fourth area $A_4$ can be linked together in a second area set in which a scaling factor $S_2$ is applied to the waveform parameter applied to the third and fourth areas $A_3$ and $A_4$ either in addition to, or in lieu of, applying the scaling factor $S_1$ to areas $A_1$ and $A_2$. FIG. 1B further illustrates that the second area $A_2$ and the third area $A_3$ can be linked together in a third area set to which a scaling factor $S_3$ is applied to the waveform parameter applied to areas $A_2$ and $A_3$. Any number of different combinations of areas and scaling factors may be implemented for controlling the waveform parameters among the different areas of one or more area sets.

Several embodiments of the method 200 are particularly useful for controlling pain perceived in different regions of the back and/or lower extremities (e.g., legs, buttocks, foot). Referring to U.S. Patent Application No. 61/176,868, filed on May 8, 2009, now expired, which is incorporated herein by reference, the electrodes can be located adjacent to vertebral bodies T9-T12, and more specifically along vertebral bodies T10-T11, for treating back and lower extremity pain. In other embodiments, however, the electrodes can be located adjacent to other vertebral bodies for treating other types of pain or other conditions.

The scaling factor can be based on a relationship between the therapy ranges of the waveform parameter for the individual areas of the patient. The therapy range for a given area can be the range of the waveform parameter that provides the desired pain control without inducing discomfort (e.g., sharp pain, adverse muscle effects, or other unwanted effects). For example, the lower limit of a therapy range for a given area can be based on the level of the waveform parameter at a sensation threshold and/or a therapeutic threshold associated with the particular area. The upper limit of the therapy range for the particular area can be based on a level of the waveform parameter at a discomfort threshold. The "sensation threshold" can be the level or range of the waveform parameter at which the patient initially senses the electrical waveform applied to the specific area. The "therapeutic threshold" can be the level or range of the waveform parameter at which the patient experiences a therapeutic effect, such as relieving pain, associated with the corresponding area. The sensation and therapeutic thresholds can be the same or similar levels of the waveform parameter. The "discomfort threshold" can be the level or range of the waveform parameter that induces pain, unwanted muscle effects, or other undesirable effects associated with the corresponding area. The lower limit of the therapy waveform may be set slightly above the sensation threshold and/or the therapeutic threshold to provide a margin that ensures the patient receives the desired therapy. Conversely, the upper limit of the therapy range can be less than the discomfort threshold to provide a margin that ensures that the patient does not experience discomfort.

The method 200 can further include setting a maximum level for the waveform parameter at each of the areas of the patient. For example, the method 200 can further include setting a first maximum of the waveform parameter for the first area and setting a second maximum of the waveform parameter for the second area. The first and second maximums of the waveform parameter can be less than the first and second discomfort thresholds, respectively. The method 200 can further include preventing the first or second levels of the waveform parameter from exceeding the first or second maximums, respectively, so that the electrical waveform does not induce undesirable side effects in any of the linked areas.

Figure 3A:
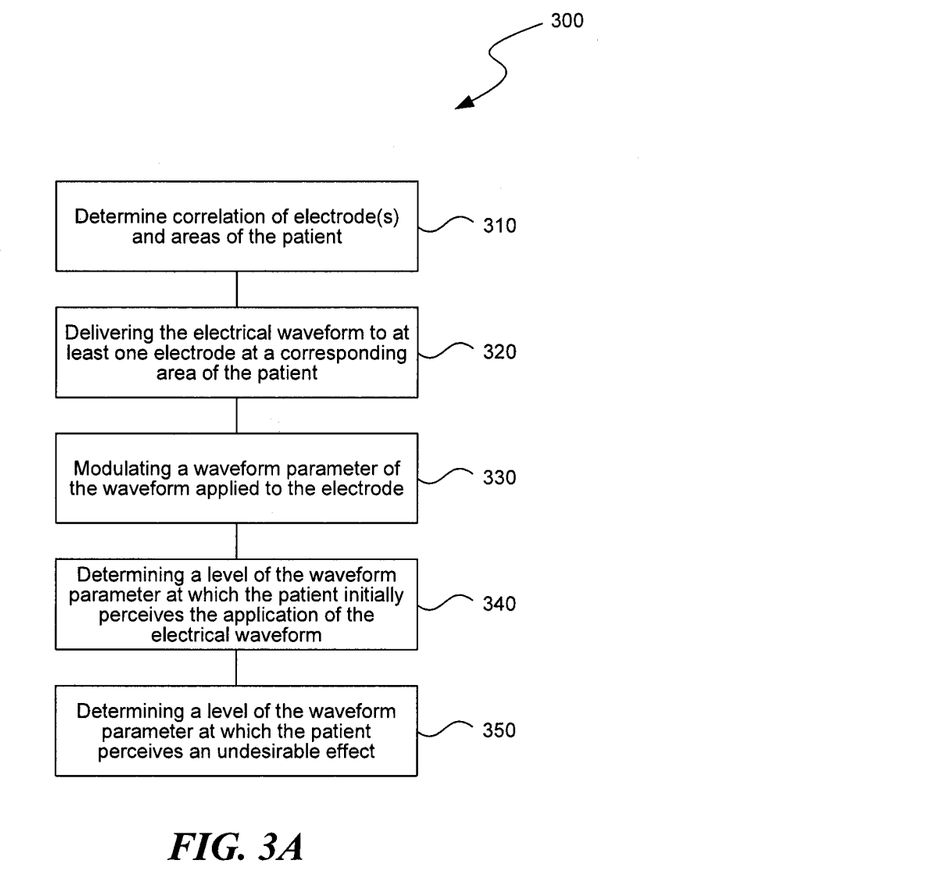
FIG. 3A is a flow diagram illustrating a routine for determining a therapy range of a waveform parameter associated with an area for use in the technology.

The therapy ranges for the individual areas of the patient can be determined during the trial period and/or throughout the therapy after final implantation. FIG. 3A is a flowchart illustrating an embodiment of a routine for determining the therapy range of the waveform parameter associated with an area of the patient. As described above, the electrodes are implanted in the patient and the electrical waveforms are generated by a waveform generator to determine whether the electrical signals provide a therapeutic effect for the specific patient. The embodiment of the routine 300 illustrated in FIG. 3A includes determining a correlation between the electrodes and the areas of the patient (block 310), delivering the electrical waveform to at least one corresponding area of the patient (block 320), and modulating a waveform parameter applied to the electrode (block 330). The correlation between the electrodes and the areas of the patient can be determined by applying the electrical waveform to one or more electrodes either individually or in various combinations with each other and recording the corresponding areas where the patient perceives a sensation, a therapeutic effect, or discomfort. Based on the modulation of the waveform parameter, the method 300 further includes determining a level of the waveform parameter at which the patient perceives the application of the electrical waveform (block 340) without discomfort and determining a level of the waveform parameter at which the patient perceives an undesirable effect (block 350). The level of the waveform parameter at which the patient perceives the application of the electrical waveform (block 340) without discomfort can correspond to the sensation threshold and/or the therapeutic threshold, and the level of the waveform parameter at which the patient perceives an undesirable effect (block 350) can correspond to the discomfort threshold. As described above, the lower and upper limits of the therapy range can be based on these thresholds.

Figure 3B:
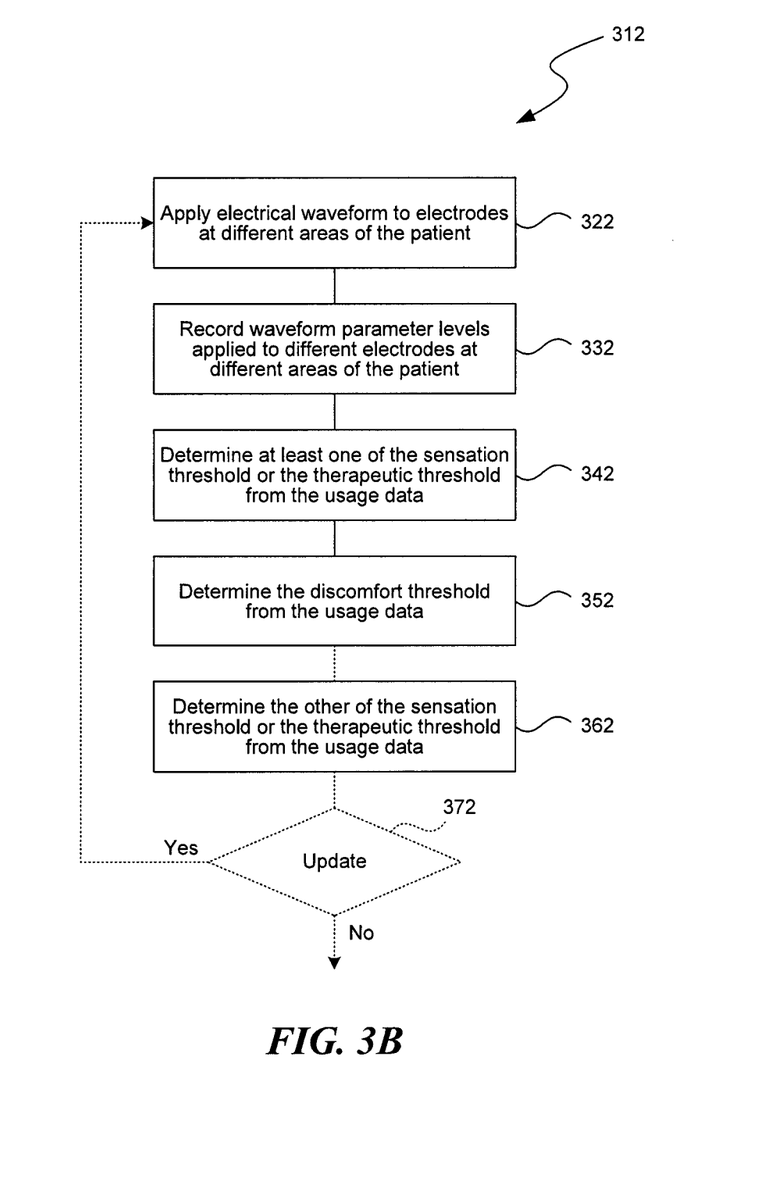
FIG. 3B is a flow diagram illustrating another routine for determining the therapy range of a waveform parameter associated with an area for use in the technology.

The therapy ranges can also be determined based on a patient usage history during the trial period and/or after final implantation of the pulse generator. FIG. 3B illustrates a routine 312 for determining the therapy range in accordance with an embodiment of the technology. In this embodiment, the routine 312 includes applying an electrical waveform to electrodes at different areas of the patient (block 322). The electrical waveform can be applied to one or more electrodes at the individual areas of the patient to determine the therapy ranges for the corresponding areas as explained above. The routine 312 further includes recording the waveform parameter levels applied to the different electrodes at the different areas of the patient (block 332) over time. The usage history of the waveform parameter can be recorded in the onboard memory of the implantable device and then downloaded via a wireless communication link to an external programmer during recharging or at other times. The routine 312 further includes determining at least one of the sensation threshold or the therapeutic threshold from the usage data (block 342) and determining the discomfort threshold from the usage data (block 352). The routine 312 can optionally including determining the other of the sensation threshold or the therapeutic threshold from the usage data (block 362) in addition to the threshold determined at block 362. The sensation threshold, discomfort threshold and/or therapeutic threshold determined from the usage data can remain static throughout the therapy, or the routine can further include updating one or more of these thresholds on a continuous or periodic basis (block 372).

The various thresholds at blocks 342, 352 and 362 can be determined by having the patient provide an input when the patient perceives a sensation, a therapeutic effect or an undesirable effect associated with the waveform. The patient inputs can be correlated with the levels of the waveform parameter to provide a series of data points for determining each of the sensation, therapeutic and/or discomfort thresholds. In a different embodiment, the thresholds can be based on an assessment of the patient's habits. For example, the lower limits of the therapy range can be determined by identifying the lower range of waveform parameter levels consistently used by the patient because such usage would indicate that the patient does not perceive the waveform or a therapeutic effect below such levels. The discomfort threshold may be assessed by ascertaining the levels of the waveform parameter at which the patient rapidly reduces the magnitude of the parameter and/or the upper range of waveform parameter levels used by the patient. A rapid reduction of the magnitude of the waveform parameter may be indicative of an acute increase in pain or other undesirable effects, whereas the upper range would indicate the patient perceives discomfort above such levels. The therapeutic threshold also may be determined by identifying the levels at which the waveform parameters are maintained for extended periods of time because this would indicate that the electrical waveform is providing the desired therapeutic effect for controlling or otherwise managing the patient's pain.

The actual linked modulation based on the relationships between the therapy ranges can be executed in a number of different ways. For example, one embodiment of the method 200 changes the level of the waveform parameter applied to the first area by a first increment and automatically changes the level of the waveform parameter applied to the second area by a second increment in direct proportion to the ratio of the first therapy range to the second therapy range. The ratio of the first therapy range to the second therapy range can be less than 1:1, equal to 1:1, or greater than 1:1 depending upon the sizes of the individual ranges. The ratio can have a positive value when the waveform parameter levels in different areas are positively correlated, and a negative value when the waveform parameter levels are negatively correlated. A negative correlation can exist, for example, when the patient experiences a stronger than desired stimulation in one area, and a weaker than desired stimulation in another area. In such instances, the scale factor can include the ratio described above, optionally modified by patient input.

When the amplitude is the waveform parameter being modulated, the ratio of the first therapy range for the first area of the patient to the second therapy range for the second area of the patient can be defined by the equation:

$$\text{Ratio} = \frac{A_{1P} - A_{1T}}{A_{2P} - A_{2T}}$$

In this equation, $A_{1P}$ is the amplitude at which the patient experiences pain at the first area, $A_{1T}$ is the amplitude at which the patient experiences a therapeutic effect at the first area, $A_{2P}$ is the amplitude at which the patient experiences pain at the second area, and $A_{2T}$ is the amplitude at which the patient experiences a therapeutic effect at the second area. In this embodiment, the change in the level of the waveform parameter applied to the second area is the product of the magnitude of the first increment that the waveform parameter was changed at the first area and the ratio of the first therapy range to the second therapy range.

Figure 4:
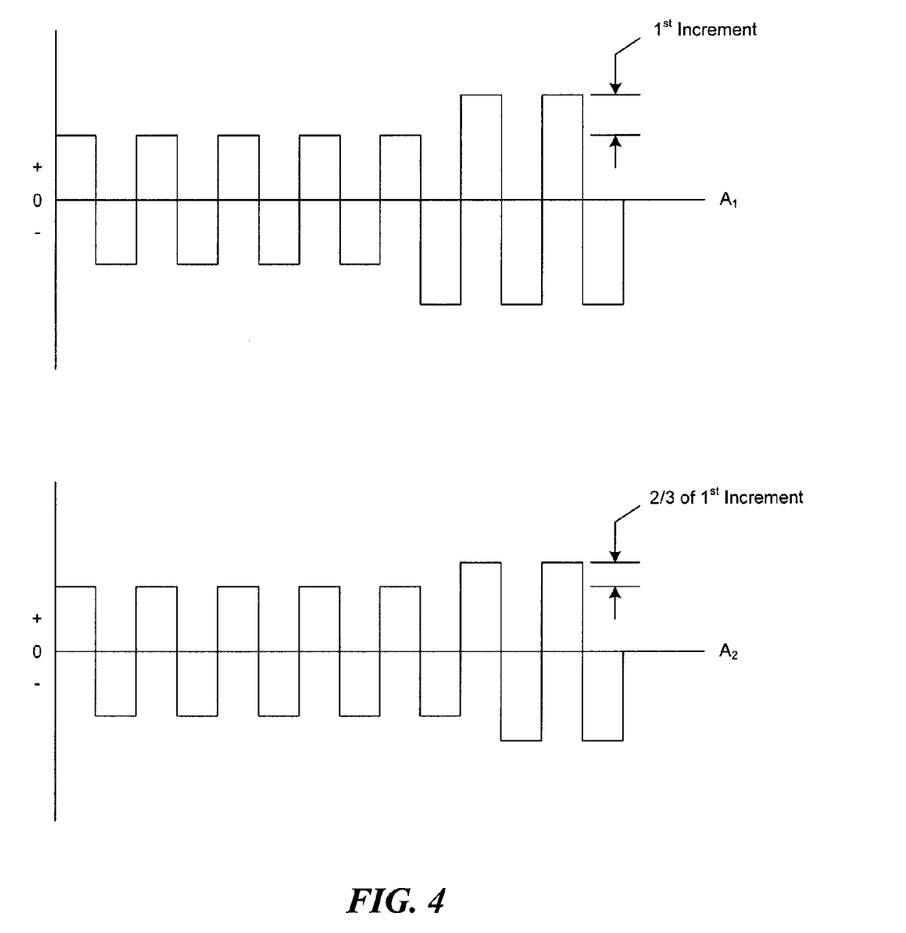
FIGS. 4 and 5 are schematic illustrations of waveforms showing implementations of methods for linked area parameter modulation in accordance with the technology.

FIG. 4 illustrates in a specific example of setting the waveform parameter applied to the second electrode in direct proportion to the therapy range ratio. The example shown in FIG. 4 is for purposes of illustration and is not limiting in any way. In this example, if the first area of the patient has a pain threshold ($A_{1P}$) of 6 mA and a therapy threshold ($A_{1T}$) of 3 mA, and if the second area of the patient has a pain threshold ($A_{2P}$) of 7 mA and a therapy threshold ($A_{2T}$) of 5 mA, then the first therapy range is 3 mA and the second therapy range is 2 mA. This results in a therapy range ratio of 3:2 based on the equation above. As a result, for every first increment that the waveform parameter is changed at the first area $A_1$, the second increment that the waveform parameter is changed at the second area $A_2$ is two-thirds of the first increment. If the therapy range ratio of the first therapy range to the second therapy range is 2:1, then the second increment is 50% of the first increment.

Figure 5:
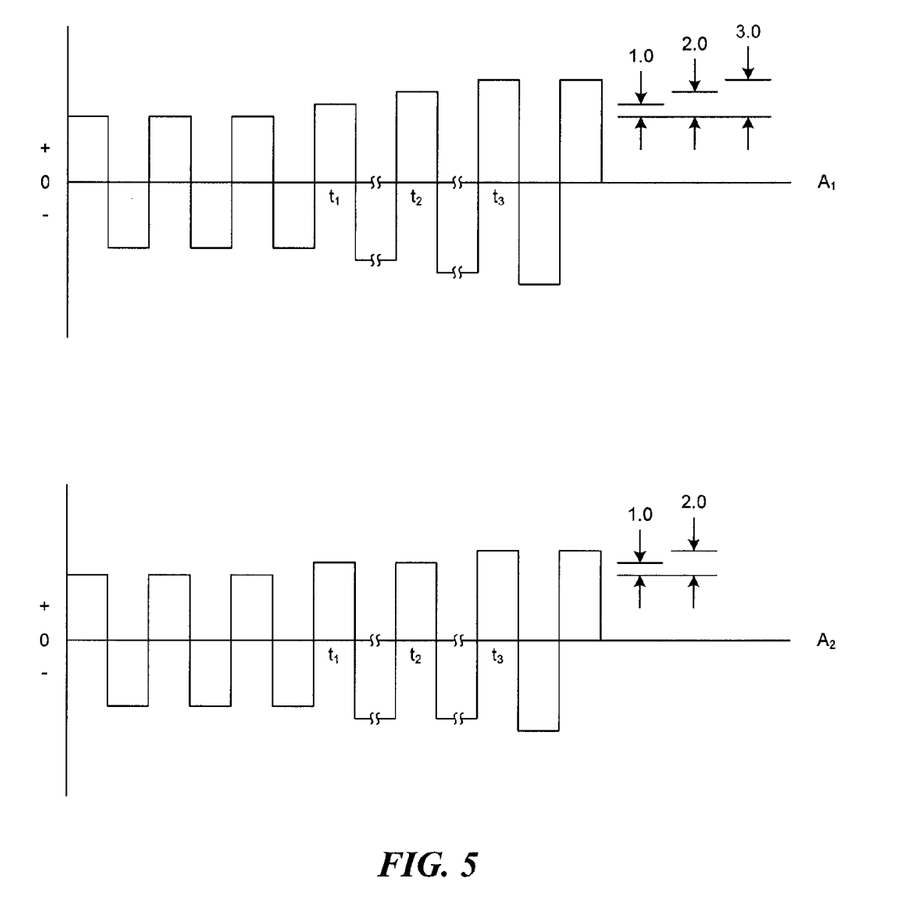

FIG. 5 illustrates another example of implementing an embodiment of the method 200 in which the levels of the waveform parameter are modulated to achieve a best-fit approximation of the relationship between the first and second therapy ranges. In this embodiment, each time the waveform parameter applied to the first electrode is changed by an incremental amount, the waveform parameter applied to the second electrode is set by either (a) changing the waveform parameter applied to the second area by the same incremental amount or (b) holding the waveform parameter applied to the second area constant. For example, when the therapy range ratio of the first therapy range to the second therapy range is 3:2 as described above, then the level of the waveform parameter applied to the second electrode is changed by two of the incremental amounts for every three incremental amounts that the level of the waveform parameter is changed at the first electrode. Stated differently, each time the patient pushes a button to increase or decrease the waveform parameter, the waveform parameter for the first electrode is changed by a full increment, but the waveform parameter is changed at the second area only every two out of three times that the patient pushes the button. FIG. 5 illustrates this point for the example of a therapy ratio of 3:2 at times $t_1$, $t_2$ and $t_3$. More specifically, when the patient pushes a button or otherwise inputs a change command using the patient programming at time $t_1$, the level of the parameter is increased by a first increment 1.0 at both the first area $A_1$ and the second area $A_2$. This provides the best fit for a 3:2 therapy ratio because the direct proportional increase at the second area $A_2$ would be approximately 0.67 such that applying an incremental change of 1.0 to area $A_2$ is closer to the therapy ratio than holding the value constant. At time $t_2$, the patient inputs another command to increase the waveform parameter by another full increment at area $A_1$ to 2.0, but the value of the waveform parameter applied to area $A_2$ is held constant. This is because after two increases of the incremental value applied to area $A_1$, the direct proportional value of the waveform parameter for area $A_2$ would be 1.33 such that holding the waveform parameter applied to the second area constant at 1.0 provides a better fit than increasing the waveform parameter applied to the second electrode to 2.0. At time $t_3$, the patient enters another input to change the waveform parameters such that the level of the waveform parameter associated with the first area $A_1$ is increased to 3.0 and the level of the waveform parameter associated with the second area $A_2$ is increased to 2.0. The foregoing examples using the ratio of 3:2 are merely for illustration, and it will be appreciated that the actual ratio of the first therapy range to the second therapy range can be any ratio depending upon the values for the first and second therapy ranges.

The method 200 can further include preventing a waveform parameter applied to the first area from exceeding a first maximum and preventing the waveform parameter applied to the second area from exceeding a second maximum. Because each area of the patient may have a different maximum for the waveform parameter, the method 200 can include determining a first maximum for the waveform parameter associated with the first area and determining a second maximum for the waveform parameter associated with the second area above which application of the waveform causes discomfort at either or both of the areas. By preventing the waveform parameter from exceeding one or both of the first and/or second maximums, the patient will not exceed the pain threshold of one area while trying to increase the amplitude applied to another area.

Figure 6:
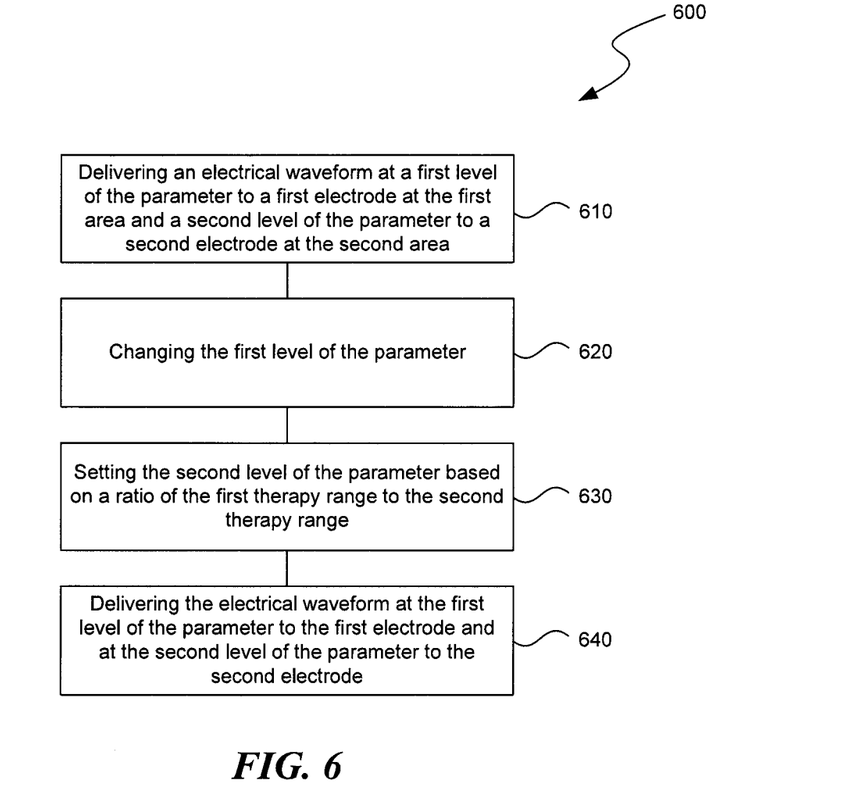
FIG. 6 is a flow diagram illustrating a process for managing pain using linked area modulation in accordance with another embodiment of the technology.

FIG. 6 is a flowchart illustrating a method 600 in accordance with another embodiment of the technology. In this embodiment, the method 600 includes delivering an electrical waveform at a first level of the waveform parameter to a first electrode at the first area and at a second level of the waveform parameter to a second electrode at the second area (block 610). The method 600 further includes changing the first level of the parameter (block 620) and setting the second level of the parameter based on a ratio of the first therapy range to the second therapy range (block 630). The electrical waveform is then delivered at the first level of the parameter to the first electrode and at the second level of the parameter to the second electrode (block 640).

Figure 7:
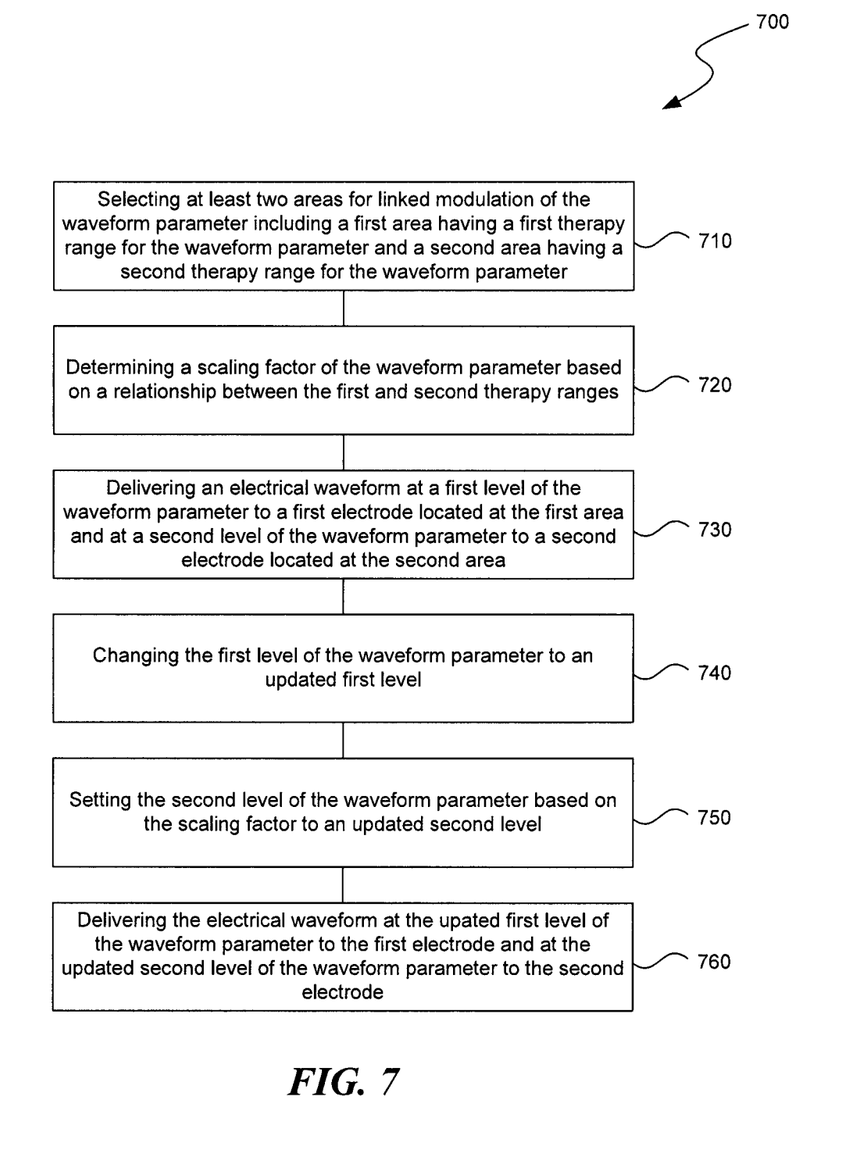
FIG. 7 is a flow diagram illustration another process for managing pain using linked area parameter modulation in accordance with a different embodiment of the technology.

FIG. 7 illustrates a method 700 in accordance with yet another embodiment of the technology. In this embodiment, the method 700 includes selecting at least two areas for linked modulation of the waveform parameter including a first area having a first therapy range for the waveform parameter and a second area having a second therapy range for the waveform parameter (block 710). The method 700 further includes determining a scaling factor of the waveform parameter based on a relationship between the first and second therapy ranges (block 720). The method 700 continues by delivering an electrical waveform at a first level of the waveform parameter to a first electrode located at the first area and at a second level of the waveform parameter to a second electrode located at the second area (block 730). The method 700 further includes changing the first level of the waveform parameter to an updated first level (block 740) and setting the second level of the waveform parameter to an updated second level based on the scaling factor and the magnitude of the change of the first level of the waveform parameter (block 750). The electrical waveform is then delivered at the updated first level of the waveform parameter to the first electrode and at the updated second level of the waveform parameter to the second electrode (block 760).

In any of the foregoing embodiments, the computer-operable medium of the system 100 can be programmed to execute any or all of the embodiments of the methods described above. Additionally, the system 100 can further comprise a memory containing a history of patient usage patterns of the waveform applied to the first and second electrodes, and the computer-operable medium can be programmed to determining whether the first area of the patient is linked to the second area of the patient. In still additional embodiments, the computer-operable medium can be programmed to determine whether the first area of the patient is not linked to the second area of the patient, and in such circumstances to change the first waveform parameter applied to the first electrode and set the second waveform parameter applied to the second electrode independently of each other.

Any of the foregoing methods and systems can include further embodiments for adapting the linked modulation of the waveform parameter to the position of the patient. For example, the system 100 can further comprise a memory including a first ratio of the first therapy range to the second therapy range associated with a first patient position and a second ratio of the first therapy range to the second therapy range associated with a second patient position. The system can further comprise a position detector, and the computer-operable medium can be programmed to change the waveform parameter applied to the first electrode and set the waveform parameter applied to the second electrode based on (a) the first ratio when the position detector indicates that the patient is in the first patient position or (b) the second ratio when the position detector indicates that the patient is in the second patient position. The position detector can comprise an accelerometer, or the position detector can comprise an impedance detector.

Several embodiments of the systems, methods and routines of the technology described above can simplify and enhance the ability to change a waveform parameter across several areas of the patient. For example, the patient can merely increase or decrease the intensity of the waveform parameter and the systems and methods automatically adjust the waveform parameter across the different areas without being limited by the area with the lowest pain threshold or the highest therapeutic threshold. As explained above, existing linked mode systems that do not provide scaling between the various areas are limited to increasing the intensity of the waveform parameter so that it does not exceed the pain threshold level of the area having the lowest pain threshold. Many embodiments of the present technology avoid or mitigate such a limitation because the scaling factor allows the intensity of the parameter to be increased differently across the areas depending on the different pain thresholds. This enables some areas to receive more intense stimulation that would otherwise cause pain in areas with lower pain thresholds. Several embodiments of the technology also maintain the relative levels of the waveform parameter over a long period of time to provide more consistent results. Existing linked mode systems change the intensity of the waveform parameter at different areas by equal increments for each change command and merely prevent the waveform parameter from exceeding an upper limit at each area, but these systems then allow the waveform parameter to be decreased from their maximums by equal increments when the patient inputs the change commands. Several embodiments of the technology avoid or mitigate this problem because the scaling factor enables the waveform parameter to be changed by different amounts at different areas. Therefore, several embodiments of the technology simplify the ongoing modulation of waveform parameters and enhance the efficacy of managing pain.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A method for programming an implantable patient treatment device, the patient treatment device including a power supply coupled to a waveform generator, the waveform generator being coupleable to an electrode device, the electrode device including a plurality of electrodes and being configured to be implanted into a patient, the method comprising:
programming the implantable treatment device with instructions that, when executed,
receive an indication of an association between (a) a first area of a patient and a first electrode of the electrode device and (b) a second area of the patient and a second electrode of the electrode device;
associate the first area with a first therapy range for a waveform parameter;
associate the second area with a second therapy range for the waveform parameter, wherein the therapy ranges are ranges of the waveform parameter that provide therapeutic effect without inducing discomfort;
change the waveform parameter applied to the first electrode; and
automatically set the waveform parameter applied to the second electrode based on a mathematical relationship between the first therapy range and the second therapy range.

2. The method of claim 1 wherein the mathematical relationship is a ratio of the first therapy range to the second therapy range.

3. A method for configuring an implantable patient treatment device, comprising:
programming the implantable treatment device with instructions that, when executed,
associate a first electrode of an implantable electrode device with a first area of a patient and with a first therapy range for a waveform parameter;
associate a second electrode of the implantable electrode device with a second area of the patient and with a second therapy range for the waveform parameter, wherein the therapy ranges are ranges of the waveform parameter that provide a therapeutic effect without inducing discomfort; and
in response to a requested change in the waveform applied to the first area or the first electrode, automatically set the waveform parameter applied to the second electrode based on a mathematical relationship between the first therapy range and the second therapy range.

4. The method of claim 3 wherein the relationship is a ratio of first therapy range to second therapy range.

5. The method of claim 3, further comprising programming the implantable treatment device with instructions that, when executed:
(a) change the waveform parameter applied to the first electrode by a first increment; and
(b) set the waveform parameter applied to the second electrode by a second increment in direct proportion to a ratio of the first therapy range to the second therapy range.

6. The method of claim 3, further comprising programming the implantable treatment device with instructions that, when executed:
(a) change the waveform parameter applied to the first electrode by a change increment for each of multiple change commands received by the implantable device; and
(b) set the waveform parameter applied to the second electrode according to a best-fit approximation of a ratio of the first therapy range to the second therapy range.

7. The method of claim 6, further comprising programming the implantable treatment device with instructions that, when executed, set the waveform parameter applied to the second electrode by changing the waveform parameter applied to the second electrode by the change increment or holding the waveform parameter applied to the second electrode constant for each of multiple change commands received by the implantable device.

8. The method of claim 3 wherein:
the waveform parameter comprises the power of the waveform, the first therapy range comprises a first power range between (a) a sensation threshold and/or a therapeutic threshold and (b) a discomfort threshold for the first area, and the second therapy range comprises a second power range between (a) a sensation threshold and/or a therapeutic threshold and (b) a discomfort threshold for the second area; and wherein the method further comprises programming the implantable treatment device with instructions that when executed:
receive a change command; and
 (a) change the power of the waveform applied to the first electrode by a first power increment; and
 (b) set the power of the waveform applied to the second electrode by a second power increment in direct proportion to a ratio of the first power range to the second power range.

9. The method of claim 3, further comprising programming the patient treatment device with instructions that, when executed, determine a ratio of the first therapy range to the second therapy range based on a history of patient usage patterns.

10. The method of claim 3, further comprising programming the patient treatment device with instructions that, when executed:
determine that the first area of the patient is not linked to the second area of the patient,
change the first waveform parameter applied to the first electrode; and
set the second waveform parameter applied to the second electrode independently of the first waveform parameter applied to the first electrode.

11. The system of claim 3, further comprising programming the patient treatment device with instructions that, when executed,
change the waveform parameter applied to the first electrode and set the waveform parameter applied to the second electrode based on (a) a first ratio of the first therapy range to the second therapy range when the patient is in a first patient position or (b) a second ratio of the first therapy range to the second therapy range when the patient is in a second patient position.

12. The system of claim 3, further comprising programming the patient treatment device with instructions that, when executed, decouple control of the waveform parameter applied to the first and second electrodes when the waveform parameter exceeds a maximum value for one of the first or second electrodes.

13. A method for configuring an implantable patient treatment device, comprising:
programming the patient treatment device with instructions that, when executed:
change a level of a waveform parameter applied to a first electrode implanted at a first area of the patient, the first area being associated with a first therapy range; and
automatically set a level of the waveform parameter applied to a second electrode, located at second area of the patient and being associated with a second therapy range, based on a scaling factor relating the first therapy range to the second therapy range.

14. The method of claim 13 wherein the scaling factor is a ratio of the first therapy range to the second therapy range.

15. The method of claim 13 wherein the therapy ranges are ranges of the waveform parameter that provide a therapeutic effect without inducing discomfort.

16. The method of claim 13, further comprising programming the patient treatment device with instructions that, when executed:
change the waveform parameter applied to the first electrode by a first increment; and
change the waveform parameter applied to the second electrode by a second increment in direct proportion to a ratio of the first therapy range to the second therapy range.

17. The method of claim 13, further comprising programming the patient treatment device with instructions that, when executed, receive a plurality of change commands, and wherein:
the scaling factor is a ratio of the first therapy range to the second therapy range;
the waveform parameter applied to the first electrode is changed by a first increment for each change command input; and
for each change command input, the waveform parameter applied to the second electrode is set by (a) changing the waveform parameter applied to the second electrode by the first increment or (b) holding the waveform parameter applied to the second electrode constant.

18. The method of claim 13, further comprising programming the patient treatment device to prevent the waveform parameter applied to the first electrode from exceeding a first maximum and preventing the waveform parameter applied to the second electrode from exceeding a second maximum.

19. The method of claim 13 wherein the waveform parameter comprises waveform amplitude.

20. The method of claim 13 wherein the waveform parameter comprises impedance between a remote electrode and each of the first electrode at the first area and the second electrode at the second area.

21. The method of claim 13 wherein the waveform parameter comprises waveform power.

22. The method of claim 13 wherein:
the first therapy range corresponds to a difference between (a) a first sensation threshold and/or a first therapeutic threshold and (b) a first discomfort threshold for the first area; and
the second therapy range corresponds to a difference between (a) a second sensation threshold and/or a second therapeutic threshold and (b) a second discomfort threshold for the second area.

23. The method of claim 13, further comprising programming the patient treatment device to:
store diagnostics including a plurality of observed patient usage patterns; and
transmit the diagnostics of observed patient usage patterns to a remote processor that determines the first therapy range, the second therapy range, and a ratio of the first therapy range to the second therapy range.

24. The method of claim 13, further comprising programming the patient treatment device with instructions that, when executed:
determine a first ratio of the first therapy range to the second therapy range associated with a first patient position;
determine a second ratio of the first therapy range to the second therapy range associated with a second patient position; and change the waveform parameter applied to the first and second electrodes based on the first ratio when the patient is in the first position or based on the second ratio when the patient is in the second position.

25. The method of claim 13, further comprising programming the patient treatment with instructions that, when executed:
receive a first maximum for the waveform parameter applied to the first electrode and set a second maximum for the waveform parameter applied to the second electrode; and
decouple the second electrode from the first electrode for adjustment of the parameter when one of the first or second electrodes has reached the first or second maximum, respectively.

* * * * *